United States Patent
Seo et al.

(10) Patent No.: US 10,822,294 B2
(45) Date of Patent: *Nov. 3, 2020

(54) DEVICE FOR REGENERATING MONO-ETHYLENE GLYCOL AND METHOD FOR REGENERATING MONO-ETHYLENE GLYCOL

(71) Applicant: SEOUL NATIONAL UNIVERSITY R&DB FOUNDATION, Seoul (KR)

(72) Inventors: Yutaek Seo, Seoul (KR); Hyunho Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/542,350

(22) Filed: Aug. 16, 2019

(65) Prior Publication Data

US 2020/0102258 A1 Apr. 2, 2020

(30) Foreign Application Priority Data

Aug. 20, 2018 (KR) .................. 10-2018-0096697

(51) Int. Cl.
C07C 29/84 (2006.01)
B01D 3/06 (2006.01)
B01D 3/14 (2006.01)

(52) U.S. Cl.
CPC ............. C07C 29/84 (2013.01); B01D 3/06 (2013.01); B01D 3/148 (2013.01)

(58) Field of Classification Search
CPC .......... C07C 29/84; B01D 3/06; B01D 3/148; B01D 3/105
See application file for complete search history.

(56) References Cited

U.S. PATENT DOCUMENTS

2020/0078702 A1* 3/2020 Seo .................. B01D 3/148

FOREIGN PATENT DOCUMENTS

| CN | 104645651 | * | 7/2018 |
| KR | 1017950030000 | | 11/2017 |

* cited by examiner

*Primary Examiner* — Yong L Chu
(74) *Attorney, Agent, or Firm* — Stuart H. Mayer; Mayer & Williams PC

(57) ABSTRACT

Provided is a device for regenerating mono-ethylene glycol (MEG) including a pre-treatment unit to receive a raw material and remove the low soluble salts therefrom, a distillation unit connected to the pre-treatment unit and configured to receive the raw material from which the low soluble salts are removed and generate a treatment solution by vaporizing the water, a flash drum connected to the distillation unit and configured to receive and vaporize at least a portion of the treatment solution, a high soluble salt removal unit connected to the flash drum and configured to remove the high soluble salts from the treatment solution, an extractor connected to the flash drum and configured to extract vaporized MEG, and a recovery unit connected to both the distillation unit and the extractor and configured to recover MEG, wherein the distillation unit includes a steam ejector into which vaporized water and external high-pressure steam flow.

17 Claims, 5 Drawing Sheets

FIG. 6

|  | $NH_4^+$ | $Li^+$ | $Na^+$ | $K^+$ | $Mg^{2+}$ | $Ca^{2+}$ | $Ba^{2+}$ | $Al^{3+}$ | $Fe^{3+}$ | $Cu^{2+}$ | $Ag^+$ | $Zn^{2+}$ | $Pb^{2+}$ |
|---|---|---|---|---|---|---|---|---|---|---|---|---|---|
| $F^-$ | sol | sol | sol | sol | insol | insol | sl sol | sol | sl sol | sol | sol | sol | insol |
| $Cl^-$ | sol | sol | sol | sol | sol | sol | sol | sol | sol | sol | insol | sol | sol |
| $Br^-$ | sol | sol | sol | sol | sol | sol | sol | sol | sol | sol | insol | sol | sl sol |
| $I^-$ | sol | sol | sol | sol | sol | sol | sol | sol |  |  | insol | sol | insol |
| $OH^-$ | sol | sol | sol | sol | insol | sl sol | sol | insol | insol | insol |  | insol | insol |
| $S^{2-}$ | sol | sol | sol | sol |  |  |  |  | insol | insol | insol | insol | insol |
| $SO_4^{2-}$ | sol | sol | sol | sol | sol | sl sol | insol | sol | sol | sol | sl sol | sol | insol |
| $CO_3^{2-}$ | sol | sol | sol | sol | insol | insol | insol |  |  |  | insol | insol | insol |
| $NO_3^-$ | sol | sol | sol | sol | sol | sol | sol | sol | sol | sol | sol | sol | sol |
| $PO_4^{3-}$ | sol | insol | sol | sol | insol | insol | insol | insol | insol | insol | insol | insol | insol |
| $CrO_4^{2-}$ | sol | sol | sol | sol | sol | sol | insol |  | insol | insol | insol | insol | insol |
| $CH_3CO_2^-$ | sol | sol | sol | sol | sol | sol | sol | sl sol | sol | sol | sol | sol | sol | sol – soluble
insol – insoluble
sl sol – slightly soluble

DEVICE FOR REGENERATING MONO-ETHYLENE GLYCOL AND METHOD FOR REGENERATING MONO-ETHYLENE GLYCOL

CROSS-REFERENCE TO RELATED APPLICATION

This application claims the benefit of Korean Patent Application No. 10-2018-0096697, filed on Aug. 20, 2018, in the Korean Intellectual Property Office, the disclosure of which is incorporated herein in its entirety by reference.

BACKGROUND

1. Field

The present invention relates to a device for regenerating mono-ethylene glycol (MEG) and a method of regenerating MEG, and more particularly, to a device for regenerating MEG in a high concentration while preventing deposition of high soluble salts in a distillation unit during an MEG regenerating process, and a method of regenerating MEG.

2. Description of the Related Art

Gas hydrates are compounds where molecules of gas such as methane, ethane, or propane are physically trapped inside cavities formed of water molecules under low temperature and high pressure conditions. While hydrocarbons are transported to the land under low temperature and high pressure conditions in deep sea gas field development, there is a high risk of formation of gas hydrates. In general, conditions for hydrate formation are moved to the low temperature and high pressure conditions by adding a thermodynamic hydrate inhibitor thereto.

Methanol and mono-ethylene glycol (MEG) are representative thermodynamic hydrate inhibitors. Since methanol that is more volatile than water is not suitable for gas fields, MEG is commonly used in the gas fields as a thermodynamic hydrate inhibitor. Although MEG having a lower volatility than water is suitable for gas fields, regeneration of MEG is essential because a large amount of MEG is required to inhibit formation of hydrates and MEG is expensive.

MEG, the simplest dihydric alcohol, is produced by hydration reaction of ethylene oxide and is a colorless, odorless, sweet-tasting, viscous liquid. In addition to controlling of formation of hydrates in the offshore gas industry, MEG may be widely used throughout the industry in an antifreeze formulation for automotive engine coolants, in an operating fluid of hydraulic brakes, as a raw material in the manufacture of polyester fibers, and as a raw material of plastics.

Two MEG regeneration processes are commonly used: the full stream concept and the slip stream concept. In the full stream concept, an MEG solution is obtained in a high concentration by removing all the salts in a single step and vaporizing water. In the slip stream concept, MEG including an appropriate amount of salts is regenerated in a high concentration by removing divalent salts by pre-treatment, vaporizing water in a distillation unit, and removing high soluble salts from a part of a flow. Since the full stream concept requires a large amount of energy consumption, the slip stream concept has been highlighted between the two types of MEG regeneration processes.

In the slip stream concept, temperature of a re-boiler needs to be maintained high to vaporize a large amount of water in a distillation unit to regenerate MEG in a high concentration. In this case, MEG is thermally degraded at the high temperature increasing a risk of performance degradation when reused as a hydrate inhibitor.

SUMMARY

The present invention has been proposed to solve various problems including the above problems, and an object of the present invention is to provide a device for regenerating mono-ethylene glycol (MEG) capable of reducing an operating temperature of a distillation unit by maintaining the distillation unit in a low vacuum state and a method of regenerating MEG.

Another object of the present invention is to provide a device for regenerating MEG in a high concentration with reduced processing costs and a method of regenerating MEG.

However, these problems to be solved are illustrative and the scope of the present invention is not limited thereby.

Additional aspects will be set forth in part in the description which follows and, in part, will be apparent from the description, or may be learned by practice of the presented embodiments.

According to an aspect of the present invention to achieve the object, provided is a device for regenerating mono-ethylene glycol (MEG) from a raw material including water, MEG, high soluble salts, and low soluble salts including a pre-treatment unit configured to receive the raw material from a raw material feeder and remove the low soluble salts therefrom, a distillation unit connected to the pre-treatment unit and configured to receive the raw material from which the low soluble salts are removed and generate a treatment solution by vaporizing the water, a flash drum connected to the distillation unit and configured to receive and vaporize at least a portion of the treatment solution, a high soluble salt removal unit connected to the flash drum and configured to remove the high soluble salts from the treatment solution, an extractor connected to the flash drum and configured to extract vaporized MEG, and a recovery unit connected to both the distillation unit and the extractor and configured to recover MEG, wherein the distillation unit includes a steam ejector into which vaporized water and external high-pressure steam flow.

According to an embodiment, the distillation unit may further include a compressor connected to both the distillation unit and the steam ejector and configured to generate high-pressure steam from a portion of vaporized water flowing from the distillation unit.

According to an embodiment, the high-pressure steam generated in the compressor may be transported to the steam ejector.

According to an embodiment, the steam ejector may maintain the inside of the distillation unit in a low vacuum state as vaporized water in the distillation unit and external high-pressure steam flow into the steam ejector.

According to an embodiment, the steam ejector may maintain the inside of the distillation unit in a low vacuum state as the vaporized water in the distillation unit and the high-pressure steam generated by the compressor flow into the steam ejector.

According to an embodiment, the low vacuum state may be maintained at a pressure of 0.4 bar to 0.6 bar.

According to an embodiment, a heating temperature of the distillation unit may be higher than a boiling point of the water and lower than a boiling point of the MEG.

According to an embodiment, the heating temperature of the distillation unit may be in the range of 120° C. to 130° C.

According to an embodiment, the high soluble salts may be monovalent salts and the low soluble salts may be divalent salts.

According to another aspect of the present invention to achieve the object, provided is a method of regenerating mono-ethylene glycol (MEG) including (a) removing the low soluble salts from the raw material;

(b) generating a treatment solution by vaporizing the water from the raw material from which the low soluble salts are removed, (c) removing the high soluble salts from the treatment solution, (d) extracting vaporized MEG from which the high soluble salts are removed, and (e) recovering the MEG, wherein the step (b) is performed in a low vacuum state as vaporized water and external high-pressure steam flow into a steam ejector of a distillation unit.

According to an embodiment, the distillation unit may further include a compressor connected to both the distillation unit and the steam ejector and configured to generate high-pressure steam using a portion of vaporized water received from the distillation unit, and the step (b) is performed in a low vacuum state as the vaporized water and the high-pressure stream generated by the compressor flow into the steam ejector.

According to an embodiment, the low vacuum state may be maintained at a pressure of 0.4 bar to 0.6 bar.

According to an embodiment, a heating temperature to vaporize water may be higher than a boiling point of the water and lower than a boiling point of the MEG in the step (b).

According to an embodiment, the heating temperature may be in the range of 120° C. to 130° C.

According to an embodiment, the high soluble salts may be monovalent salts and the low soluble salts may be divalent salts.

According to an embodiment of the present invention as described above, the effect of decreasing an operating temperature of the distillation unit may be obtained by maintaining the distillation unit in a low vacuum state.

In addition, according to an embodiment of the present invention, the effect of reducing processing costs and regenerating MEG in a high concentration may be obtained.

However, the scope of the present invention is not limited by these effects.

BRIEF DESCRIPTION OF THE DRAWINGS

These and/or other aspects will become apparent and more readily appreciated from the following description of the embodiments, taken in conjunction with the accompanying drawings in which:

FIG. 6 is a table showing high soluble salts and low soluble salts separately.

DETAILED DESCRIPTION

Figure 1:
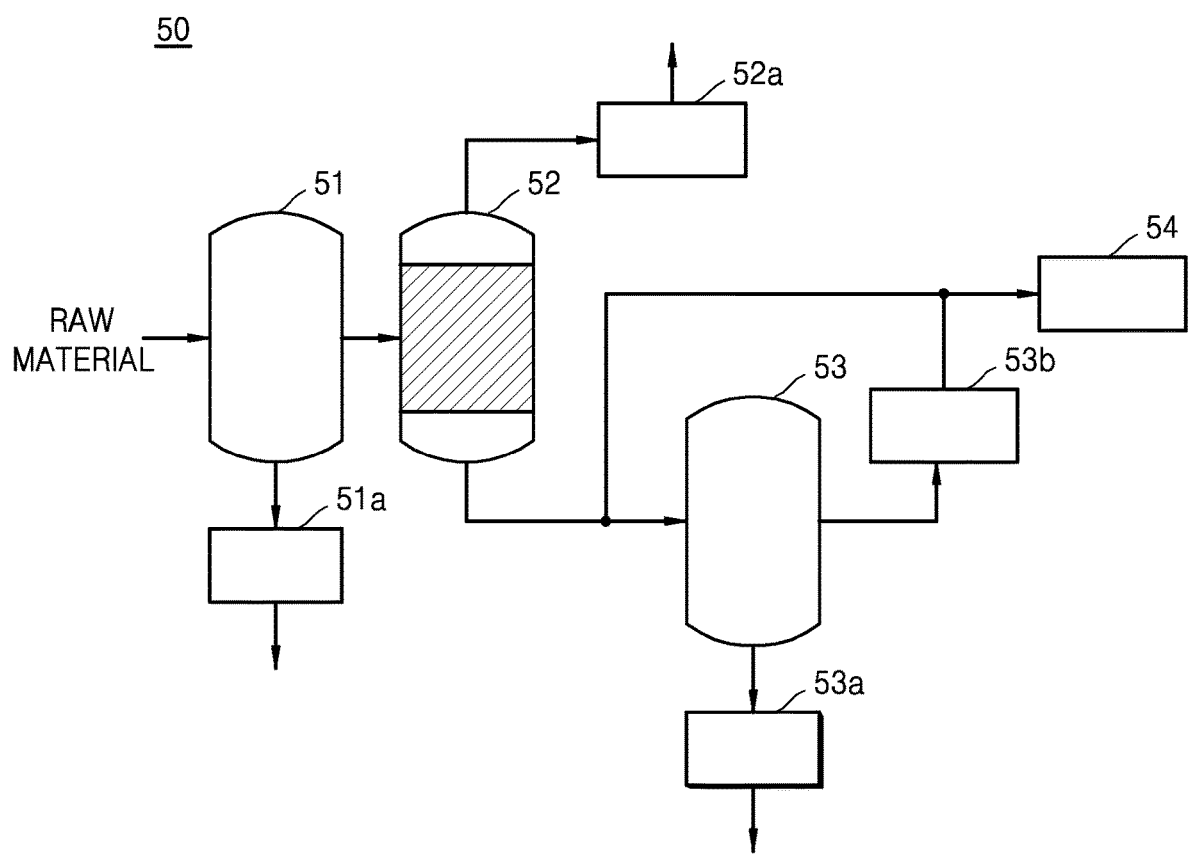
FIG. 1 is a schematic diagram illustrating a conventional slip stream-type mono-ethylene glycol (MEG) regeneration device.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein, in connection with one embodiment, may be implemented within other embodiments without departing from the spirit and scope of the invention. In addition, it is to be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views and length, areas, thicknesses, and shapes of elements in the drawings may be exaggerated for descriptive convenience.

Hereinafter, embodiments of the present invention will be described in detail with reference to the accompanying drawings so that these embodiments may be readily implemented by those skilled in the art.

FIG. 1 is a schematic diagram illustrating a conventional slip stream-type mono-ethylene glycol (MEG) regeneration device 50.

Referring to FIG. 1, the slip stream-type MEG regeneration device 50 includes a pre-treatment unit 51, a distillation unit 52, a flash drum 53, and a recovery unit 54. A process of regenerating MEG by a slip stream method is as follows.

First, when a raw material is supplied, the pre-treatment unit 51 removes low soluble salts. The removed low soluble salts may be discharged to the outside via a low soluble salt removal unit 51a. Subsequently, the distillation unit 52 separates water from MEG. Water may be discharged to the outside via a water discharge unit 52a. Subsequently, a predetermined amount of MEG is bypassed to be vaporized through the flash drum 53, and high soluble salts are removed therefrom. The high soluble salts may be discharged to the outside through a high soluble salt removal unit 53a. MEG vaporized in the flash drum 53 may pass through an MEG extractor 53b and join a mainstream of MEG flowing from the distillation unit 52, and then recovered by the recovery unit 54 at a high concentration.

Although the conventional slip stream method may increase energy efficiency, processing costs are excessively high because a high temperature of a re-boiler needs to be maintained to vaporize a large amount of water in the distillation unit 52.

Figure 2:
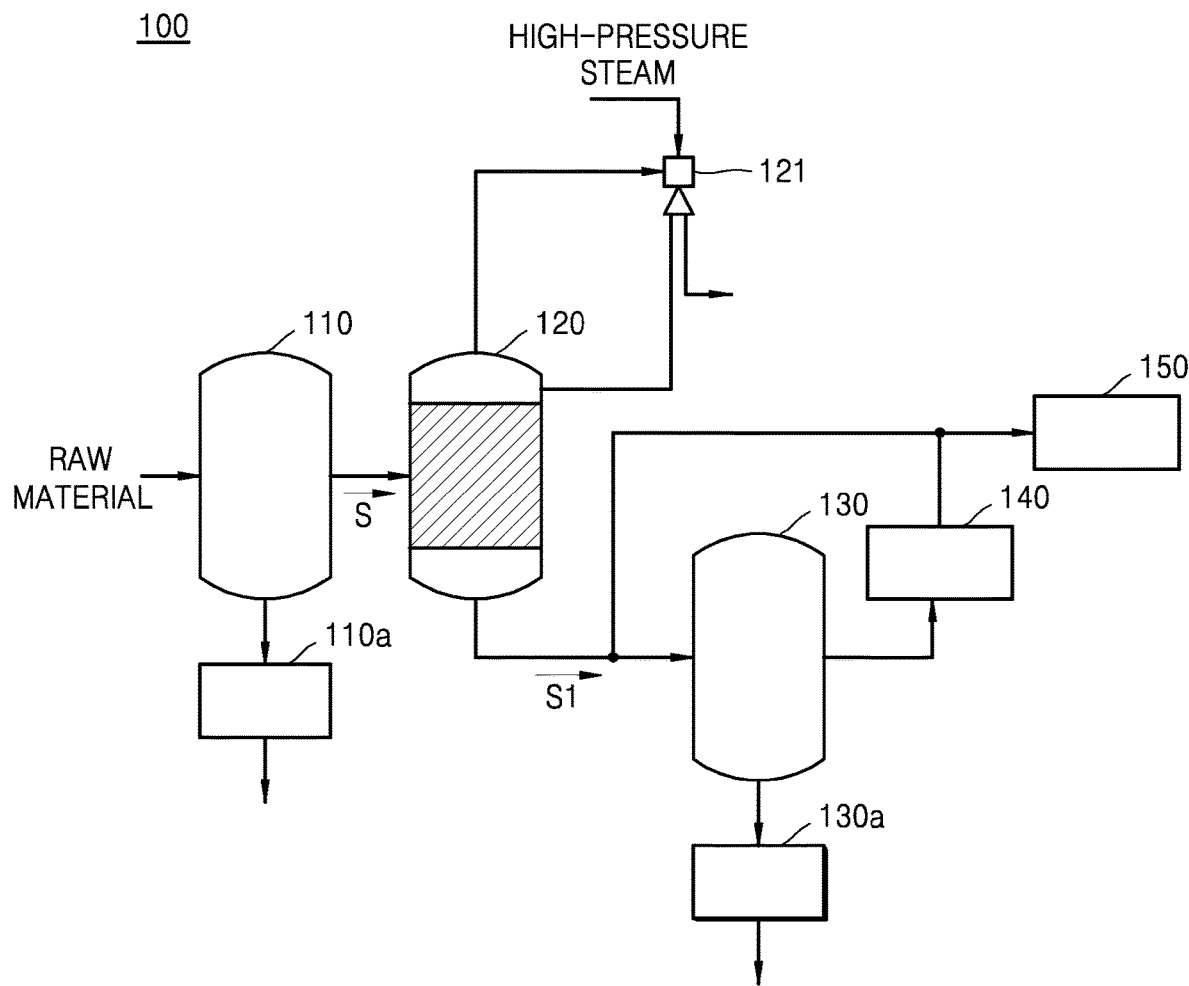
FIG. 2 is a schematic diagram illustrating an MEG regeneration device according to an embodiment of the present invention.

FIG. 2 is a schematic diagram illustrating a device for regenerating MEG (MEG regeneration device) according to an embodiment of the present invention.

An MEG regeneration device 100 according to the present invention is a device for regenerating MEG applied to apparatuses for developing deep-sea gas fields and used to inhibit formation of hydrates. An operating temperature of a distillation unit may be reduced by maintaining the distillation unit in a low vacuum state so that processing costs may be reduced and MEG may be obtained in a high concentration.

To this end, the MEG regeneration device 100 according to an embodiment of the present invention is a device for regenerating MEG from a raw material including water, mono-ethylene glycol (MEG), high soluble salts, and low soluble salts. The MEG regeneration device 100 includes a pre-treatment unit 110 configured to remove low soluble salts from the raw material received from a raw material feeder, a distillation unit 120 connected to the pre-treatment unit 110 and configured to generate a treatment solution by vaporizing water from the raw material from which the low soluble salts are removed, a flash drum 130 connected to the distillation unit 120 and configured to remove high soluble salts from the treatment solution, an extractor 140 connected to the flash drum 130 and configured to extract vaporized MEG from which the high soluble salts are removed, and a recovery unit 150 connected to the extractor 140 and configured to recover MEG, wherein the distillation unit 120 includes a steam ejector 121 into which vaporized water and external high-pressure steam flow.

In addition, a method of regenerating MEG according to an embodiment of the present invention, as a method of regenerating MEG from a raw material including water, MEG, high soluble salts, and low soluble salts, includes (a) removing the low soluble salts from the raw material, (b) generating a treatment solution by vaporizing water from the raw material from which the low soluble salts are removed, (c) removing the high soluble salts from the treatment solution, (d) extracting the vaporized MEG from which the high soluble salts are removed, and (e) recovering MEG. Here, the step (b) is processed in a low vacuum state since the vaporized water and external high-pressure steam flow into a steam ejector of the distillation unit.

Specifically, referring to FIG. 2, the MEG regeneration device 100 according to an embodiment of the present invention includes the pre-treatment unit 110, the distillation unit 120, the flash drum 130, the extractor 140, and the recovery unit 150.

The raw material may include water, MEG, high soluble salts, and low soluble salts. As used herein, the high soluble salts refer to salts easily dissolved in water when compared with the low soluble salts with a solubility increasing as temperature increases and mainly include monovalent salts such as NaCl, KCl, and NaOH. The low soluble salts refer to salts hardly dissolved in water with a solubility decreasing as temperature increases and mainly include divalent salts such as $CaCo_3$, $CaSO_4$, $BaSO_4$, and $BaCO_3$. Referring to FIG. 6, salts marked with "soluble" may belong to the high soluble salts, and salts marked with "insoluble" or "slightly soluble" may belong to the low soluble salts.

The pre-treatment unit 110 may receive the raw material from a raw material feeder (not shown) and remove the low soluble salts therefrom. The pre-treatment unit 110 may include a tank (not shown) to contain the raw material and a heater (not shown) to heat the raw material. Since the solubility of the low soluble salts decreases as temperature increases, the heater may heat the raw material to precipitate the low soluble salts. The precipitated low soluble salts may be discharged to the outside through the low soluble salt removal unit 110a. The low soluble salt removal unit 110a may include a centrifuge (not shown), a filter (not shown), and the like to treat the low soluble salts precipitated as solids or may include a circulation pipe (not shown), a pump (not shown), and the like to circulate the raw material back to the tank of the pre-treatment unit 110. In addition, the pre-treatment unit 110 may further include any known component to remove the low soluble salts.

The distillation unit 120 may be connected to the pre-treatment unit 110 and receive the raw material (or flow) S from which the low soluble salts are removed to vaporize water contained in the raw material S. Throughout the specification, the solution obtained after water is vaporized in the distillation unit 120 is referred to as a treatment solution S1.

The distillation unit 120 may be formed as a distillation column and evaporate or vaporize water contained in the raw material S from which the low soluble salts are removed by fractional distillation. The distillation unit 120 may vaporize water under atmospheric pressure and may perform heating at a temperature higher than a boiling point of water to vaporize water.

Vaporized water in the distillation unit 120 may be discharged to the outside through the steam ejector 121.

As described above, the conventional slip stream-type MEG regeneration device 50 shown in FIG. 1 has a problem that the temperature of the re-boiler is maintained high since a large amount of water is vaporized only in the distillation unit 52.

On the contrary, the MEG regeneration device 100 according to the present invention further includes the steam ejector 121 to reduce a heating temperature (operating temperature) of the distillation unit 120. The steam ejector 121 is connected to the distillation unit 120, and the distillation unit 120 is maintained in a low vacuum state as vaporized water in the distillation unit 120 and external high-pressure steam flow into the steam ejector 121.

The steam ejector 121 is a type of pump obtaining the same effect as the pump by using high-pressure steam as a power source. While the high-pressure steam passes through the steam ejector 121, the pressure of the distillation unit 120 decreases to a low vacuum state.

More specifically, the high-pressure steam is sprayed into a chamber of the steam ejector 121, and vaporized water (sucked fluid) flows at a high speed through a narrow passage together with the high-pressure steam to form a very low pressure, and accordingly the pressure of the distillation unit 120 decreases to the low vacuum state.

Thus, in the present invention, the steam ejector 121 is connected to the distillation unit 120 and maintains the distillation unit 120 in the low vacuum state by using the high-pressure steam obtained from the outside and the vaporized water obtained in the distillation unit 120. In this regard, the low vacuum state may be a vacuum state having a pressure in the range of 0.4 bar to 0.6 bar.

In order to vaporize water in the distillation unit 120, the heating temperature of the distillation unit 120 may be higher than a boiling point of water and lower than a boiling point of MEG. More specifically, the heating temperature of the distillation unit 120 may be in the range of 120° C. to 130° C.

Figure 4:
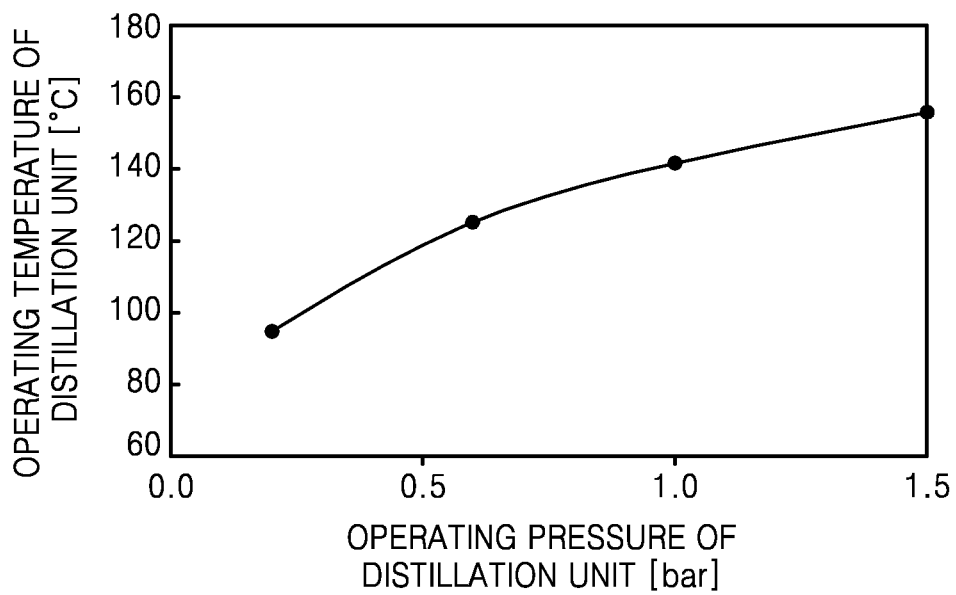
FIG. 4 is a graph illustrating operating temperatures (heating temperatures) required to regenerate MEG in a high concentration according to operating pressure of the distillation unit.

FIG. 4 is a graph illustrating operating temperatures (heating temperatures) required to regenerate MEG in a high concentration according to operating pressure of the distillation unit.

Referring to FIG. 4, in the case of the conventional slip steam-type method, operation conditions of the distillation unit include a pressure of about 1 bar to 1.5 bar and a very high heating temperature (operating temperature) of 140° C. to 165° C. Because thermal degradation of MEG may occur at a temperature around 160° C., performance of regenerated and reinjected MEG as a hydrate inhibitor may deteriorate.

However, in the case of the slip stream-type method according to the present invention, the distillation unit 120 may be maintained in a low vacuum state, e.g., at a pressure of 0.4 bar to 0.6 bar, thereby reducing the heating temperature (operating temperature) of the distillation unit 120 to the range of 120° C. to 130° C.

The flash drum 130 is connected to the distillation unit 120 and may receive at least a portion of the treatment solution S1 from the distillation unit 120. Also, the flash drum 130 may remove high soluble salts from the treatment solution S1.

More specifically, a predetermined amount of the treatment solution S1 flowing out from the distillation unit 120 bypasses and flows into the flash drum 130, and MEG is vaporized therein in a high temperature and low pressure environment. In a high-temperature and low-pressure environment, MEG contained in the treatment solution S1 may be evaporated and exist in a gaseous state, and the high soluble salts may exist in a sludge state. The sludge of the high soluble salts may be discharged to the outside through a high soluble salt discharge unit 130*a* connected to the flash drum 130.

The extractor 140 may be connected to the flash drum 130 and receive MEG vaporized in the gaseous state from the flash drum 130. The MEG in the gaseous state may be cooled and liquefied.

The recovery unit 150 may be connected to both of the distillation unit 120 and the extractor 140 and receive MEG treated by the extractor 140 in a high concentration.

Also, the treatment solution S1 flowing out of the distillation unit 120 and MEG treated in the extractor 140 may be combined in the recovery unit 150, and thus MEG may be recovered in a high concentration.

Figure 3:
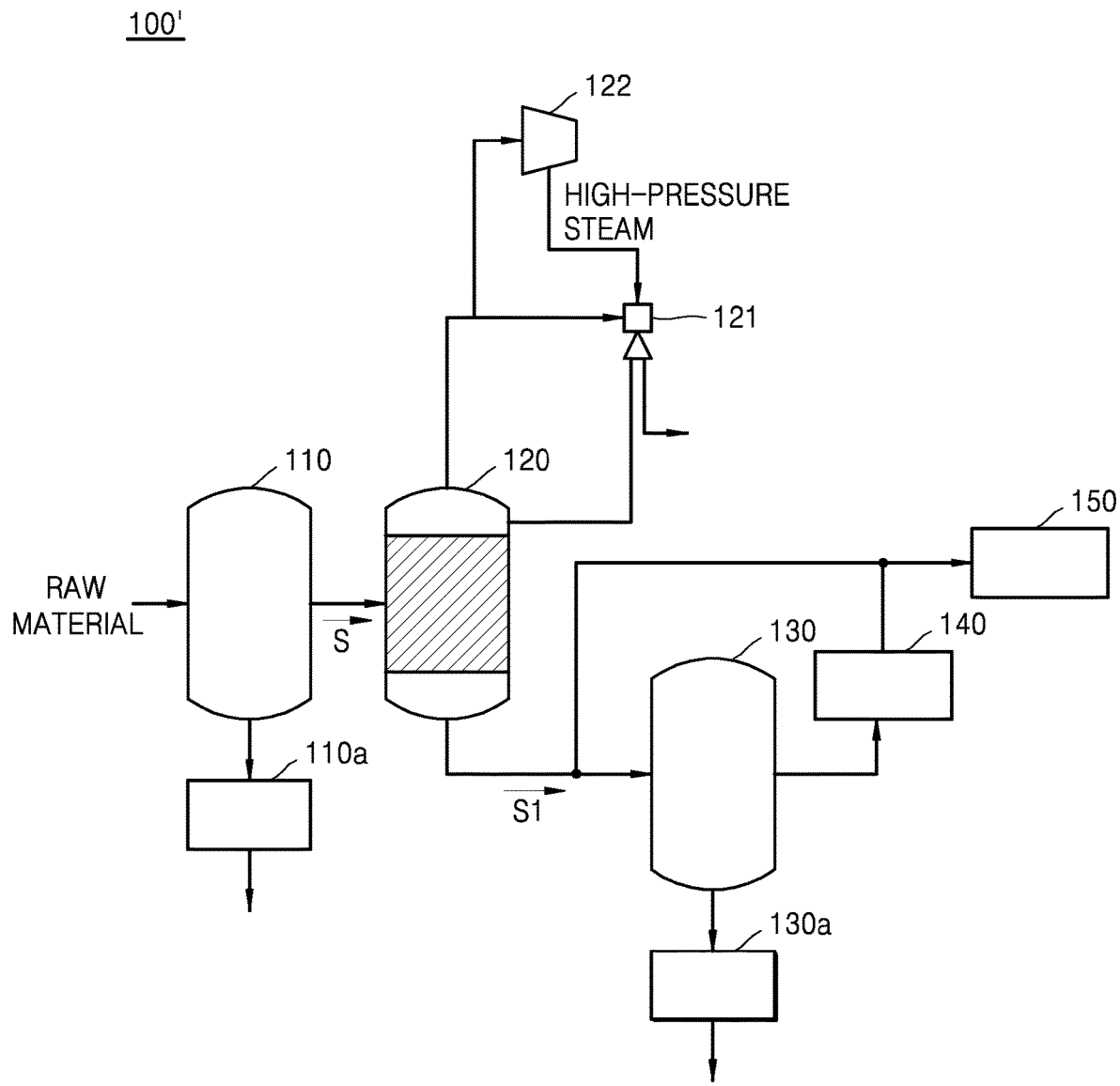
FIG. 3 is a schematic diagram illustrating an MEG regeneration device according to another embodiment of the present invention.

FIG. 3 is a schematic diagram illustrating an MEG regeneration device 100' according to another embodiment of the present invention. Since the configuration shown in FIG. 3 is the same as that shown in FIG. 2 with the same reference numerals, detailed descriptions thereof will be omitted and only differences will be described.

Referring to FIG. 3, a compressor 122 may further be connected to both the distillation unit 120 and the steam ejector 121. The compressor 122 may receive a part of vaporized water from the distillation unit 120 and generate high-pressure steam by using the compressor 122. The high-pressure steam generated in the compressor 122 is transported to the steam ejector 121. In this case, since water produced in the distillation unit 120 is converted into high-pressure steam and used, the effect of reducing operating costs may be obtained by using the high-pressure steam.

Figure 5:
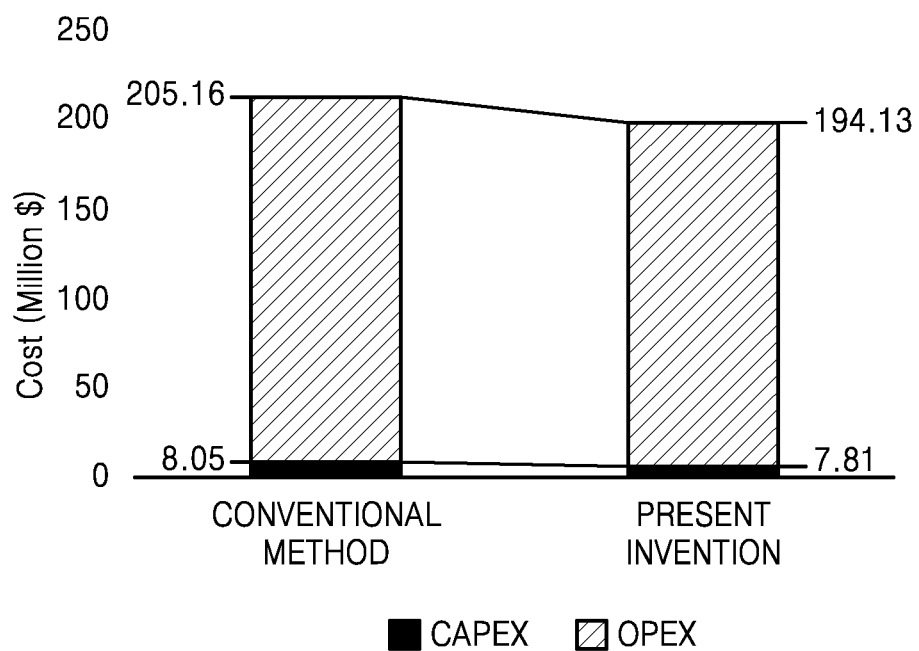
FIG. 5 illustrates evaluation results of economic feasibility of the MEG regeneration device according to an embodiment of the present invention.

FIG. 5 illustrates evaluation results of economic feasibility of the MEG regeneration device according to an embodiment of the present invention.

CAPEX refers to all of the costs a company spends to purchase and install equipment and the like, and OPEX refers to operating costs in consideration of energy consumption for 15 years. The unit is Million $.

Referring to FIG. 5, a conventional technology exhibits a CAPEX of 8.05 and an OPEX of 205.16, and the technology according to the present invention exhibits a CAPEX of 7.81 and an OPEX of 194.13. A total cost according to the conventional method is 213.21 and a total cost according to the present invention is 200.38 decreased from that of the conventional method by about 6%.

As described above, according to the present invention, the distillation unit may be maintained in a low vacuum state, resulting in a decreased operating temperature of the distillation unit. Also, according to an embodiment of the present disclosure, processing costs may be reduced and MEG may be regenerated in a high concentration.

While exemplary embodiments have been shown and described above, it will be apparent to those skilled in the art that modifications and variations could be made without departing from the scope of the present invention as defined by the appended claims.

What is claimed is:

1. A device for regenerating mono-ethylene glycol (MEG) from a raw material comprising water, MEG, high soluble salts, and low soluble salts, the device comprising:
a pre-treatment unit configured to receive the raw material from a raw material feeder and remove the low soluble salts therefrom;
a distillation unit connected to the pre-treatment unit and configured to receive the raw material from which the low soluble salts are removed and generate a treatment solution by vaporizing the water;
a flash drum connected to the distillation unit and configured to receive and vaporize at least a portion of the treatment solution;
a high soluble salt removal unit connected to the flash drum and configured to remove the high soluble salts from the treatment solution;
an extractor connected to the flash drum and configured to extract vaporized MEG; and
a recovery unit connected to both the distillation unit and the extractor and configured to recover MEG,
wherein the distillation unit comprises a steam ejector into which vaporized water and external high-pressure steam flow.

2. The device according to claim 1, wherein the distillation unit further comprises a compressor connected to both the distillation unit and the steam ejector and configured to generate high-pressure steam from a portion of vaporized water flowing from the distillation unit.

3. The device according to claim 2, wherein the high-pressure steam generated in the compressor is transported to the steam ejector.

4. The device according to claim 1, wherein the steam ejector maintains the inside of the distillation unit in a low vacuum state as vaporized water in the distillation unit and external high-pressure steam flow into the steam ejector.

5. The device according to claim 2, wherein the steam ejector maintains the inside of the distillation unit in a low vacuum state as the external high-pressure steam and the high-pressure steam generated by the compressor flow into the steam ejector.

6. The device according to claim 4, wherein the low vacuum state is maintained at a pressure of 0.4 bar to 0.6 bar.

7. The device according to claim 1, wherein a heating temperature of the distillation unit is higher than a boiling point of the water and lower than a boiling point of the MEG.

8. The device according to claim 7, wherein the heating temperature of the distillation unit is in the range of 120° C. to 130° C.

9. The device according to claim 1, wherein the high soluble salts are monovalent salts and the low soluble salts are divalent salts.

10. A method of regenerating mono-ethylene glycol (MEG) from a raw material comprising water, MEG, high soluble salts, and low soluble salts, the method comprising:

(a) removing the low soluble salts from the raw material;
(b) generating a treatment solution by vaporizing the water from the raw material from which the low soluble salts are removed;
(c) removing the high soluble salts from the treatment solution;
(d) extracting vaporized MEG from which the high soluble salts are removed; and
(e) recovering the MEG,
wherein the step (b) is performed in a low vacuum state as vaporized water and external high-pressure steam flow into a steam ejector of a distillation unit.

11. The method according to claim 10, wherein the distillation unit further comprises a compressor connected to both the distillation unit and the steam ejector and configured to generate high-pressure steam using a portion of vaporized water received from the distillation unit, and the step (b) is performed in a low vacuum state as the vaporized water and the high-pressure stream generated by the compressor flow into the steam ejector.

12. The method according to claim 10, wherein the low vacuum state is maintained at a pressure of 0.4 bar to 0.6 bar.

13. The method according to claim 10, wherein a heating temperature to vaporize water is higher than a boiling point of the water and lower than a boiling point of the MEG in the step (b).

14. The method according to claim 13, wherein the heating temperature is in the range of 120° C. to 130° C.

15. The method according to claim 10, wherein the high soluble salts are monovalent salts and the low soluble salts are divalent salts.

16. The device according to claim 5, wherein the low vacuum state is maintained at a pressure of 0.4 bar to 0.6 bar.

17. The method according to claim 12, wherein the low vacuum state is maintained at a pressure of 0.4 bar to 0.6 bar.

* * * * *